US00PP27441P3

(12) United States Plant Patent
Nelson et al.

(10) Patent No.: US PP27,441 P3
(45) Date of Patent: Dec. 6, 2016

(54) STRAWBERRY PLANT NAMED 'DILIGENT'

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 21 days.

(21) Appl. No.: 14/121,354

(22) Filed: Aug. 25, 2014

(65) Prior Publication Data

US 2016/0057904 P1 Feb. 25, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'DILIGENT'. This new strawberry plant named 'DILIGENT' is primarily adapted to the growing conditions of the central coast of California, and is primarily characterized by its large fruit size, small calyx, early fruit production, medium to small plant size, fruiting trusses held above the plant, and short fruiting trusses.

4 Drawing Sheets

BACKGROUND OF THE INVENTION

The present invention relates to a new and distinct strawberry variety named 'DILIGENT'. This new variety is a result of a controlled cross made in 2004 in an ongoing breeding program between strawberry variety designated 'BG-959' (U.S. Plant Pat. No. 17,864) and strawberry variety designated 'BG-2010' (a non-patented selection). Due to the combining of the reciprocal seed lots, it is unknown as to which parent variety is the seed parent and which parent variety is the pollen parent. The variety is botanically known as *Fragaria ananassa*.

The seedling resulting from the aforementioned cross was selected from a controlled breeding plot in Ventura County, California in the winter of 2006. After its selection, the new variety was asexually propagated by stolons in both Siskiyou County, California and San Joaquin County, California. The new variety was extensively tested over the next several years in fruiting fields in Ventura County, California. This propagation has demonstrated that the combination of traits disclosed herein as characterizing the new variety are fixed and remain true-to-type through successive generations of asexual reproduction.

BRIEF SUMMARY OF THE INVENTION

'DILIGENT' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'DILIGENT', which in combination distinguish this strawberry plant as a new and distinct variety:

1. Large fruit size;
2. Small calyx;
3. Early fruit production;
4. Medium to small plant;
5. Fruiting trusses held above the plant; and
6. Short fruiting trusses.

The strawberry variety that is believed to be most closely related to the new variety 'DILIGENT' is 'BG-959' (U.S. Plant Pat. No. 17,864). In side-by-side comparisons to the similar strawberry variety 'BG-959', 'DILIGENT' differs by the following combination of characteristics as described in Table 1.

TABLE 1

| Characteristic | 'DILIGENT' | 'BG-959' (U.S. Plant Pat. No. 17,864) |
|---|---|---|
| Fruit: size (grams) | 35.4 (large) | 27.2 (medium) |
| Fruit: color of internal flesh | Medium red | Ranges from medium to dark red |
| Fruit: size of calyx relative to fruit diameter | Slightly smaller | Slightly larger |
| Fruit: hollow center expression | Absent or very weak | Ranges from moderate to strong |
| Plant: habit | Upright | Semi-upright |
| Plant: density | Ranges from medium to sparse | Medium |
| Foliage: color | Medium yellow green | Ranges from medium to dark green |
| Fruiting truss: anthocyanin intensity | Absent or very weak | Medium |
| Fruiting truss: position relative to foliage | Above | Level with |

For identification, a series of molecular markers have been determined for this new variety.

'DILIGENT' differs from its parents, 'BG-959' and 'BG-2010' by the following combination of characteristics as described in Table 2.

TABLE 2

| Characteristic | 'DILIGENT' | 'BG-959' (U.S. Plant Pat. No. 17,864) | 'BG-2010' |
|---|---|---|---|
| Marketable yield (gm/plant) | 1,098 | 1,058 | 900 |
| Fruit size | Large | Medium | Ranges from medium to large |
| Plant size | Ranges from medium to small | Ranges from medium to small | Ranges from medium to large |
| Fruit color | Red | Red | Ranges from red to dark red |

BRIEF DESCRIPTIONS OF THE PHOTOGRAPHS

The accompanying color photographs illustrate the overall appearance of typical specimens of the new strawberry variety 'DILIGENT' at various stages of development, as true as it is reasonably possible with color reproductions of this type. Color in the photographs may differ slightly from the color value cited in the botanical descriptions which accurately describe the color of 'DILIGENT'. The depicted plant and plant parts of the new strawberry variety 'DILIGENT' are approximately five to six months old. The photographs were taken in Ventura County, California.

DETAILED BOTANICAL DESCRIPTION

Figure 1:
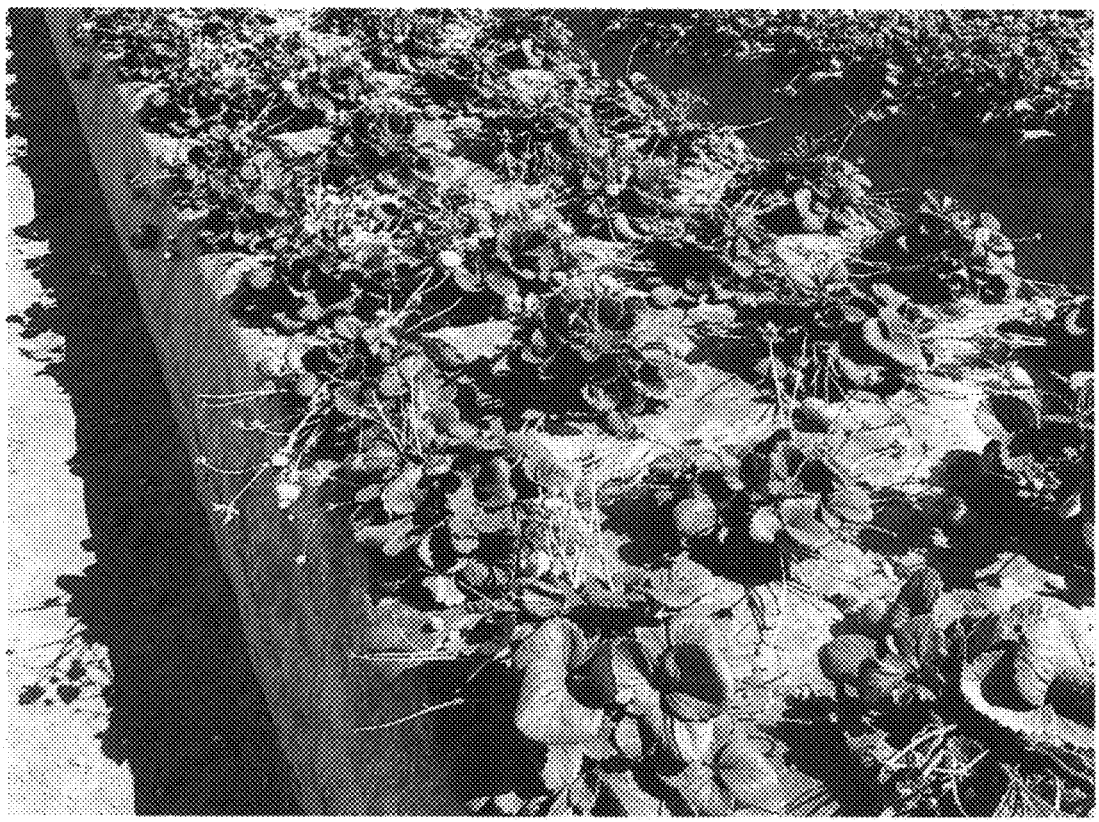
FIG. 1 shows typical fruiting field characteristics of 'DILIGENT', taken in the month of April 2014.
Figure 2:
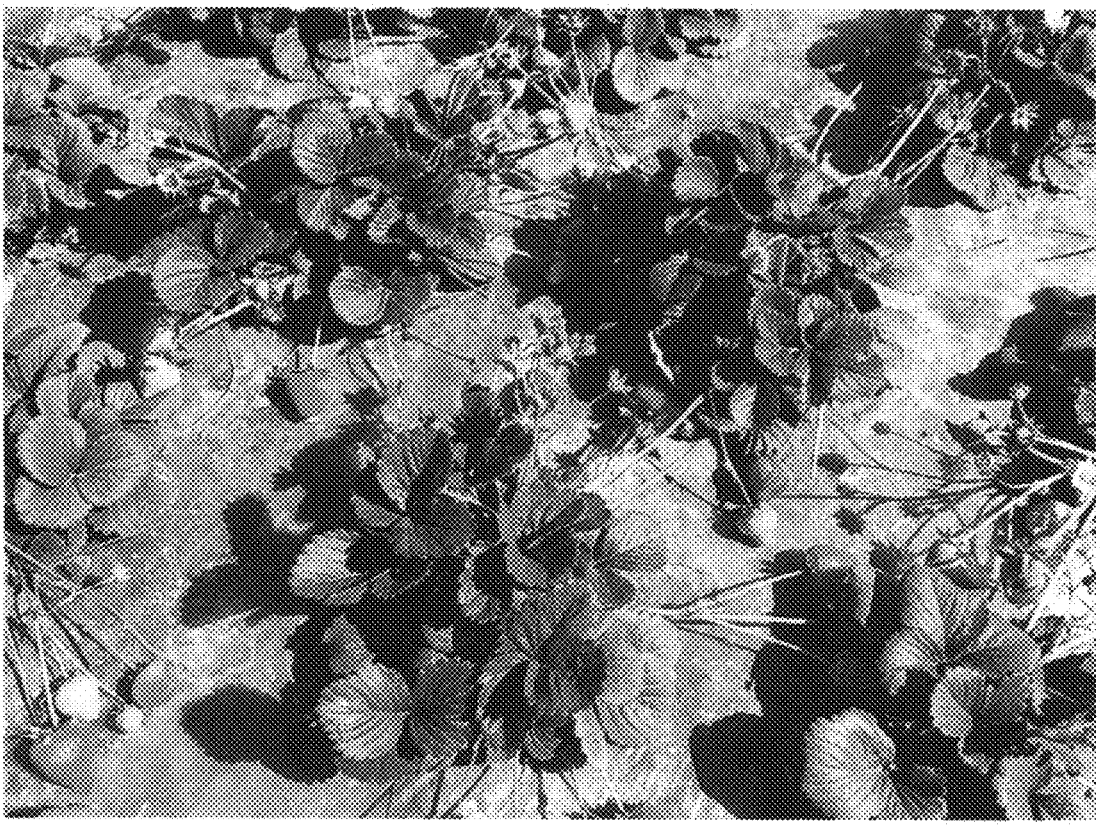
FIG. 2 shows a close-up view of the typical leaf structure of 'DILIGENT', taken in the month of April 2014.
Figure 3:
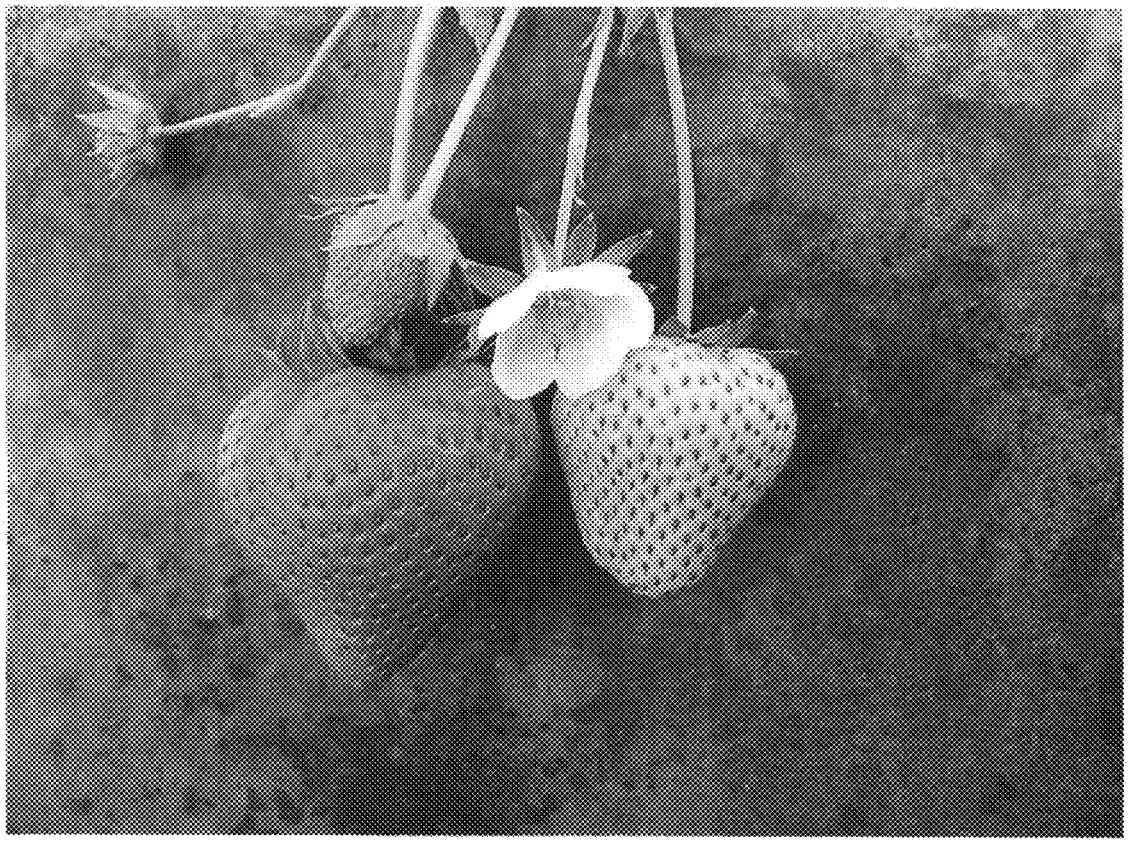
FIG. 3 shows typical mature and immature field fruit of 'DILIGENT', taken in the month of March 2014.
Figure 4:
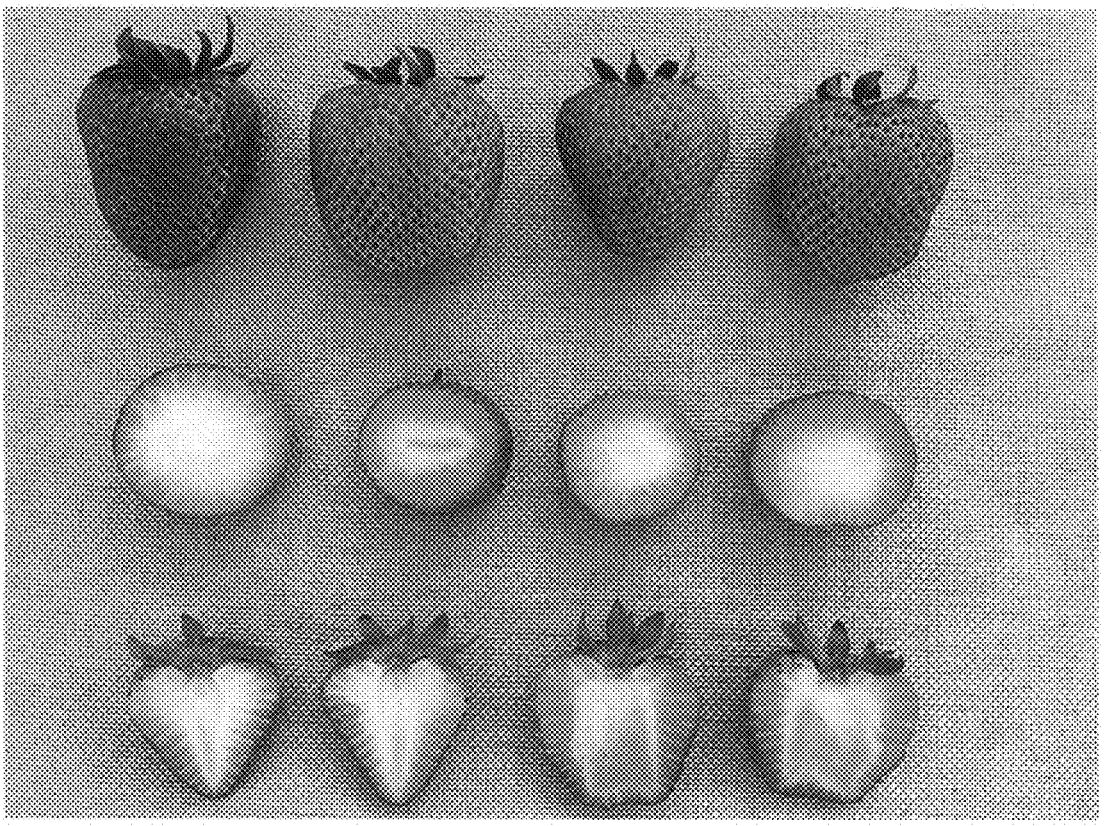
FIG. 4 shows typical internal and external mature fruit characteristics of 'DILIGENT', taken in the month of March 2014.

The new variety 'DILIGENT' has not been observed under all possible environmental conditions. The characteristics of the new variety 'DILIGENT' may vary in detail, depending upon variations in environmental factors, including weather (temperature, humidity and light intensity), day length, soil type and location. In addition, the characteristics of any parental variety or comparison variety included in Tables 3 through 9 of the present invention may vary in detail, depending upon variations in environmental factors, including weather (temperature, humidity and light intensity), day length, soil type and location.

The aforementioned photographs, together with the following description of the new variety 'DILIGENT', unless otherwise noted, are based on observations taken during the 2014 growing season in Ventura County, California. These measurements and ratings were taken from plants of 'DILIGENT' dug from a high-elevation nursery located in Siskiyou County, California during early October 2013 and planted approximately four to five days later in Ventura County, California. The approximate age of the observed plants is five to six months. Yield observations and fruit quality characteristics are averaged from five years of data collected from the 2010 through 2014 growing seasons. Flower measurements and characteristics are from secondary flowers unless otherwise noted. Fruit characteristics and measurements are from secondary fruit, unless otherwise noted.

Color terminology where noted follows The Royal Horticultural Society Colour Chart, London (2007).

The following Tables 3 through 9 describe fruit, plant, stolon, foliage, fruiting truss, flower, and pest and disease characteristics of the new strawberry 'DILIGENT'.

TABLE 3

FRUIT CHARACTERISTICS

| Characteristic | 'DILIGENT' |
|---|---|
| Color of mature fruit | RHS 46B, red |
| Color of internal flesh | RHS 44A, medium red |
| Color of core | RHS 38A, light red |
| Fruit length (cm) | 4.5 |
| Fruit width (cm) | 4.2 |
| Fruit size | Very large |
| Fruit length/width ratio | 1.07, slightly longer than broad |
| Calyx diameter (cm) | 3.8 |
| Average fruit weight (gm) | 35.4 |
| Achene color, shaded side | RHS 153B, yellow green group |
| Achene color, sun-exposed side | RHS 183A, greyed purple group |
| Achene weight (mg) | 0.40 |
| Average achenes per berry | 396 |
| Marketable fruit yield (gm/plant) | 1,098 |
| Predominant fruit shape | Conical |
| Difference in shapes between primary and secondary fruit | Moderate |
| Band without achenes | Absent or very narrow |
| Evenness of fruit surface | Even or very slightly uneven |
| Evenness of fruit color | Even or very slightly uneven |
| Fruit glossiness | Ranges from medium to strong |
| Insertion of achenes | Level with surface |
| Position of calyx attachment | Inserted |
| Attitude of sepals | Ranges from downward to outward |
| Size of calyx relative to fruit diameter | Slightly smaller |
| Adherence of calyx (when fully ripe) | Strong |
| Firmness of fruit flesh | Medium |
| Distribution of red color of the flesh | Marginal and central |
| Hollow center expression | Absent or very weak |
| Fruit flavor | Good |
| Soluble solids (% Brix) | 7.6 |
| Time of first flower | Early |
| Time of first harvest | Early |
| Harvest period | January to June |
| Harvest maturity | Early season |
| Type of bearing | Not remontant (short day) |

TABLE 4

PLANT CHARACTERISTICS

| Characteristic | 'DILIGENT' |
|---|---|
| Plant height (cm) | 13.1 |
| Plant spread (cm) | 27.0 |
| Plant size | Ranges from small to medium |
| Plant habit | Upright |
| Plant density | Ranges from sparse to medium |
| Plant vigor | Medium |

TABLE 5

STOLON CHARACTERISTICS

| Characteristic | 'DILIGENT' |
|---|---|
| Stolon color | RHS 146D, yellow green group |
| Stolon anthocyanin coloration | RHS 180D, greyed red group |
| Stolon anthocyanin intensity | Absent or very weak |
| Stolon pubescence | Medium |
| Attitude of hairs | Upward |
| Average stolon quantity | Medium |
| Average stolon diameter at bract (mm) | 3.0 |

TABLE 6

| FOLIAGE CHARACTERISTICS | |
|---|---|
| Characteristic | 'DILIGENT' |
| Foliage: | |
| Color of upper surface | RHS 146A, medium yellow green |
| Color of underside | RHS 137C, yellow green group |
| Number of leaflets | 3 |
| Shape in cross section | Slightly concave to flat |
| Interveinal blistering | Medium |
| Leaf glossiness | Medium |
| Leaf variegation | Absent |
| Terminal Leaflet: | |
| Length (cm) | 6.3 |
| Width (cm) | 5.6 |
| Leaf size | Ranges from medium to small |
| Length/width ratio | 1.11, longer than broad |
| Shape of base | Obtuse |
| Margins (shape of teeth) | Rounded (crenate) |
| Serrations per leaf | 19.4 |
| Petiole: | |
| Petiole color | RHS 144A, yellow green group |
| Petiole length (cm) | 8.7 |
| Petiole diameter (mm) | 3.2 |
| Petiolule color | RHS 144A, yellow green group |
| Petiolule length (mm) | 7.6 |
| Attitude of hairs | Strongly outward |
| Petiole pubescence | Heavy |
| Stipule: | |
| Color | RHS 146A, yellow green group |
| Anthocyanin coloration | RHS 161B, red purple group |
| Anthocyanin intensity | Medium |
| Length (mm) | 13.5 |
| Width (mm) | 10.8 |

TABLE 7

| FRUITING TRUSS CHARACTERISTICS | |
|---|---|
| Characteristic | 'DILIGENT' |
| Anthocyanin coloration | RHS 181D, greyed red group |
| Anthocyanin intensity | Absent or very weak |
| Length at maturity (cm) | 26.0 |
| Position relative to foliage | Above |
| Number of flowers | Medium |
| Pedicel attitude of hairs | Upward |

TABLE 7-continued

| FRUITING TRUSS CHARACTERISTICS | |
|---|---|
| Characteristic | 'DILIGENT' |
| Pubescence | Medium |
| Attitude at first pick | Prostrate |

TABLE 8

| FLOWER CHARACTERISTICS | |
|---|---|
| Characteristic | 'DILIGENT' |
| Petal color | RHS NN155C, white group |
| Sepal color | RHS 137B, green group |
| Receptacle color | RHS 147B, yellow green group |
| Anther color | RHS 13A, yellow group |
| Corolla diameter (mm) | 32.5, large |
| Calyx diameter (mm) | 33.9 |
| Petal length (mm) | 11.0 |
| Petal width (mm) | 12.1 |
| Petal length/width ratio | 0.90, broader than long |
| Petals per flower | 5.6 |
| Sepal length (mm) | 11.1 |
| Sepal width (mm) | 4.6 |
| Sepal length/width ratio | 2.43 |
| Sepals per flower | 11.3 |
| Size of calyx relative to corolla | Larger |
| Relative position of petals | Overlapping |
| Stamen | Present |
| Size of inner calyx relative to outer calyx | Ranges from smaller to same |

TABLE 9

| PEST AND DISEASE REACTIONS | |
|---|---|
| Characteristic | 'DILIGENT' |
| Powdery mildew | Moderately susceptible |
| *Verticillium* wilt | Moderately susceptible |
| Angular leaf spot | Susceptible |
| *Botrytis* fruit rot | Moderately susceptible |
| Two-spotted spider mite | Moderately susceptible |

We claim:

1. A new and distinct strawberry plant named 'DILIGENT', as herein described and illustrated by the characteristics set forth above.

* * * * *